US012605138B2

(12) United States Patent
Parag et al.

(10) Patent No.: US 12,605,138 B2
(45) Date of Patent: Apr. 21, 2026

(54) DEVICE AND A METHOD FOR MONITORING AN IMPLANT

(71) Applicants: IMEC VZW, Leuven (BE); Katholieke Universiteit Leuven, Leuven (BE); Stichting IMEC Nederland, Eindhoven (NL)

(72) Inventors: Anirudh Kumar Parag, Leuven (BE); Bogdan Raducanu, Heverlee (BE); Chris Van Hoof, Leuven (BE); Nick Van Helleputte, Korbeek-Dijle (BE); Stefano Stanzione, Veldhoven (NL)

(73) Assignees: Katholieke Universiteit Leuven, Leuven (BE); Stichting IMEC Nederland, Eindhoven (NL)

( * ) Notice: Subject to any disclaimer, the term of this patent is extended or adjusted under 35 U.S.C. 154(b) by 0 days.

(21) Appl. No.: 18/965,088

(22) Filed: Dec. 2, 2024

(65) Prior Publication Data

US 2025/0186017 A1     Jun. 12, 2025

(30) Foreign Application Priority Data

Dec. 6, 2023   (EP) ..................................... 23214539

(51) Int. Cl.
   A61B 8/00       (2006.01)
   A61B 8/08       (2006.01)
   G01S 5/22       (2006.01)
(52) U.S. Cl.
   CPC .............. A61B 8/0841 (2013.01); G01S 5/22 (2013.01)

(58) Field of Classification Search
   CPC ... A61B 8/0841; A61B 8/4236; A61B 8/4477; A61B 8/4483; A61B 8/4209; G01S 5/22
   See application file for complete search history.

(56) References Cited

U.S. PATENT DOCUMENTS

| | | | |
|---|---|---|---|
| 2009/0198295 A1 | 8/2009 | Dennis et al. | |
| 2010/0106028 A1 | 4/2010 | Penner et al. | |
| 2016/0268813 A1* | 9/2016 | Reynolds | ............... H04B 11/00 |
| 2017/0360399 A1* | 12/2017 | Rothberg | ................. A61B 8/12 |
| 2018/0226838 A1* | 8/2018 | Govindaraj | .......... A61N 1/3787 |

OTHER PUBLICATIONS

Wang, et al: "Ultrasonic Implant Localization for Wireless Power Transfer: Active Uplink and Harmonic Backscatter", 2019 IEEE International Ultrasonics Symposium, Glasgow, Scotland, pp. 818-821, 2019.

(Continued)

*Primary Examiner* — Joel Lamprecht
(74) *Attorney, Agent, or Firm* — MOSER TABOADA

(57) ABSTRACT

A device for monitoring an implant comprises: an array of ultrasound transducer elements configured to receive a localization ultrasound signal from the implant; and a signal processor configured to, for each ultrasound transducer element of at least a subset of ultrasound transducer elements, identify a time point corresponding to a peak intensity of the received localization ultrasound signal at the ultrasound transducer element, wherein relative time delays between the time points identified for the ultrasound transducer elements form information relating to a location of the implant.

13 Claims, 3 Drawing Sheets

(56)                    References Cited

OTHER PUBLICATIONS

Benedict, et al: "Phased Array Beamforming Methods for Powering Biomedical Ultrasonic Implants", IEEE Transactions on Ultrasonic, Ferroelectrics, and Frequency Control, vol. 69, No. 10, pp. 2756-2765, 2022.

Meng, et al: "Self-Image-Guided Ultrasonic Wireless Power Transmission to Millimeter-Sized Biomedical Implants", Annual International Conference of the IEEE Engineering in Medicine and Biology Society, pp. 364-367, 2019.

Saccher, et al: "Time-efficient low power time/phase-reversal beamforming for the tracking of ultrasound implantable devices", 2022 IEEE International Ultrasonics Symposium, Venice, Italy, pp. 1-4, 2022.

Extended European Search Report for Application No. EP23214539.1 dated May 21, 2024, 6 pages.

* cited by examiner

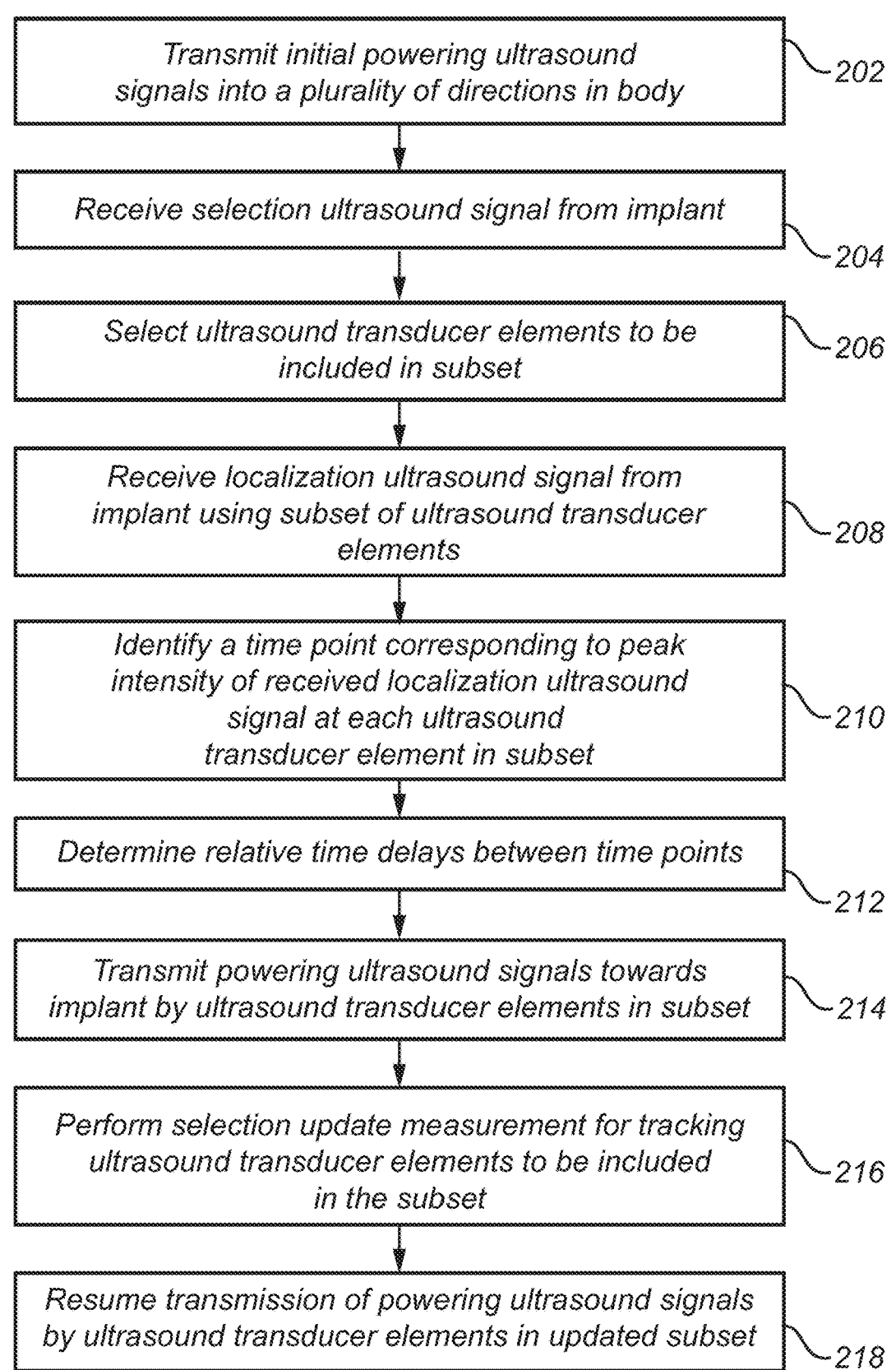

Transmit initial powering ultrasound
signals into a plurality of directions in body                    ⌐202

Receive selection ultrasound signal from implant                 ⌐204

Select ultrasound transducer elements to be
included in subset                                               ⌐206

Receive localization ultrasound signal from
implant using subset of ultrasound transducer
elements                                                         ⌐208

Identify a time point corresponding to peak
intensity of received localization ultrasound
signal at each ultrasound
transducer element in subset                                     ⌐210

Determine relative time delays between time points               ⌐212

Transmit powering ultrasound signals towards
implant by ultrasound transducer elements in subset             ⌐214

Perform selection update measurement for tracking
ultrasound transducer elements to be included
in the subset                                                    ⌐216

Resume transmission of powering ultrasound signals
by ultrasound transducer elements in updated subset             ⌐218

*Fig. 3*

DEVICE AND A METHOD FOR MONITORING AN IMPLANT

CROSS-REFERENCE TO RELATED APPLICATIONS

The present application claims the benefit of and priority to EP patent application Ser. No. 23/214,539.1, filed Dec. 6, 2023, the entire contents of which is incorporated herein by reference.

TECHNICAL FIELD

The present description relates to monitoring of an implant. The monitoring of the implant may be used for localizing, powering and/or tracking of the implant.

BACKGROUND

Implants are increasingly used in numerous applications. For instance, implants may be used for controlling a body function within a body of a living being, such as a human being or an animal. Implants may also or alternatively be used for performing measurements within the body to gather information, which may, e.g., be used for monitoring a health condition of the living being.

The miniaturization of implants still remains a major challenge. This is largely attributed to the need for storing energy which may be accomplished with batteries. Hence, energy storage becomes a milestone bottleneck towards developing medical devices that could be implanted employing minimally invasive surgeries.

In addition, lifetime of implants may be limited by limited battery life. Thus, in order to enable miniaturization and to increase lifetime of implants, it would be desired to provide powering of implants from outside the body. However, there is a need to provide efficient powering of implants, limiting an amount of radiative energy being transmitted into the body so as to meet regulation requirements.

Further, in many applications, it is desired to provide powering of implants from a battery-powered device, which may for instance be wearable by the living being. This implies that the powering of the implant may be performed without affecting everyday life of a user. However, since a battery-powered device may need to be used for powering of implants, there is also a need for providing an efficient process in the device sued for powering of implants.

SUMMARY

An objective of the present description is to provide robust and efficient monitoring of an implant. A particular objective of the present description is to provide robust localization of the implant, whereby a determined location of the implant may be used for controlling efficient powering of the implant.

These and other objectives are at least partly met by the invention as defined in the independent claims. Preferred embodiments are set out in the dependent claims.

According to a first aspect, there is provided a device for monitoring an implant; said device comprising: an array of ultrasound transducer elements configured to receive a localization ultrasound signal from the implant; a signal processor configured to, for each ultrasound transducer element of at least a subset of ultrasound transducer elements, identify a time point corresponding to a peak intensity of the received localization ultrasound signal at the ultrasound transducer element, wherein relative time delays between the time points identified for the ultrasound transducer elements form information relating to a location of the implant.

The device is configured to detect time points corresponding to peak intensity of the received localization ultrasound signal. It is realized that the peak intensity may be identified in a robust manner compared to, for instance, determining a start time or an end time of an ultrasound signal. Start or end time of the ultrasound signal may be more prone to errors due to unwanted reflections of the ultrasound signal affecting determination of the time point and due to a time point of a relatively weak signal strength being determined. Thus, by using peak intensity, the device allows time points representing receipt of the localization ultrasound signal to be robustly determined for the ultrasound transducer elements.

The identified time points indicate when the localization ultrasound signal is received at the respective ultrasound transducer elements. This provides information of the location of the implant, since an ultrasound transducer element receiving the localization ultrasound signal before another ultrasound transducer element is closer to the implant.

Further, it is possible to use analog processing blocks for determining the time points. This implies that there is no need to use analog-to-digital converters (ADCs) for processing the received localization ultrasound signal in order to enable determining a location of the implant. Thanks to avoiding use of ADCs for digitization of the received ultrasound signal, power consumption may be limited.

The identified time points provide information relating to the location of the implant. However, according to an embodiment, the device may further be configured to determine relative time delays between the time points identified for the ultrasound transducer elements.

This implies that the device may not only identify the time points but may also determine the relative time delays. The determination of the relative time delays may be performed by the signal processor. Alternatively, the time points identified by the signal processor may be indicated to another element for allowing the relative time delays to be determined. Thus, the time points may be provided to a control unit, which may process the time points in digital domain for determining the relative time delays. However, it should be realized that the control unit may only need to receive indications of the time points from the signal processor, such that the localization ultrasound signal does not need to be converted into digital domain.

Thus, the device may be configured to determine relative time delays for the subset of ultrasound transducer elements. This implies that the device need only store time delays and need not store entire received ultrasound signals. Hence, the device has limited memory requirements.

It is further realized that the use of ultrasound is suitable for wireless powering of implants. Thus, by using ultrasound transducer elements for determining information relating to a location of the implant, the same ultrasound transducer elements may also be used for powering the implants. Ultrasound allows for output of highly directive signals, which implies that a powering signal may radiate energy such that the radiated energy is directed towards the implant and may be efficiently used. Further, ultrasound has a relatively low attenuation in the body of the living being, such that ultrasound may be used for localization and powering of implants deep within the body.

The ultrasound signal is a signal that propagates as an acoustic wave having a frequency above 20 kHz. According to an embodiment, a frequency above 500 kHz may be used, such as a frequency within a range of 500 kHz-10 MHz.

The implant is configured to be arranged in a living being. For instance, the implant may be arranged in the living being through surgery or by being swallowed. Once implanted, the implant may not be accessible, or not easily accessible (e.g., only through surgery or other invasive method), such that it may be desired to monitor the implant from another device. The device for monitoring of the implant may thus be configured to monitor the implant from outside the body of the living being. However, it should be realized that the device may also be arranged within the living being, such as being arranged externally to an organ within which the implant is arranged.

The device is configured to monitor an implant. This implies that the device is configured to collect information relating to the implant. The device may also be configured to provide signals to the implant, such as for powering of the implant and/or for controlling functions of the implant. The device is at least configured to determine information relating to the location of the implant. This information may be used at least for directing powering of the implant. It may also be used for following the implant within the body and for ensuring that the implant is properly placed in the body.

The array of ultrasound transducer elements may be a one-dimensional array. The one-dimensional array may be used for determining the location of the implant in relation to a line defined by the one-dimensional array. The array may preferably be a two-dimensional array, which may allow for more accurately determining the location of the implant within three dimensions in the body.

The ultrasound transducer element is configured to receive the localization ultrasound signal. The ultrasound transducer element may be configured to detect the ultrasound signal. For instance, the ultrasound transducer element may generate an electrical signal in response to the received and detected ultrasound signal, wherein the electrical signal facilitates further processing of the received ultrasound signal. The ultrasound transducer element may be configured in any manner for converting the received ultrasound signal to an electrical signal. For instance, the ultrasound transducer element may comprise a diaphragm sensitive to vibrations of the ultrasound signal, wherein detected vibrations may be converted to an electrical signal using capacitance, piezoelectricity, or an optical signal. The ultrasound transducer element may be a capacitive micromachined ultrasonic transducer, a piezoelectric micromachined ultrasonic transducer, an optical micromachined ultrasound sensor, or a bulk-driven piezoelectric transducer.

The signal processor may be configured to process electrical signals formed by the ultrasound transducer elements based on the ultrasound transducer elements receiving and detecting the localization ultrasound signal.

The signal processor may be configured to process the analog electrical signals. The signal processor may comprise passive components (such as capacitors, resistors, and inductors) and/or active components (such as transistors and operational amplifiers) in order to process electrical signals. The signal processor may be configured to identify a peak intensity in the received localization ultrasound signal so as to allow a time point of the peak intensity to be determined. This is a relatively simple processing of the received signal such that the signal processor may be implemented in analog domain and, hence, the signal processor may be an analog signal processor.

The signal processor may be connected to the array of ultrasound transducer elements for receiving a detected localization ultrasound signal from the ultrasound transducer elements. The signal processor may be directly electrically connected to the array of ultrasound transducer elements. For instance, the signal processor may be integrated with the array of ultrasound transducer elements on a common substrate.

The subset of the ultrasound transducer elements may be a subset among the ultrasound transducer elements of the array. By using only a subset of ultrasound transducer elements, power consumption may be reduced. The subset of ultrasound transducer elements may be selected based on selecting which ultrasound transducer elements are active to detect the localization ultrasound signal, or by selecting which detected signals to be processed by the signal processor.

It should be further realized that in some embodiments the signal processor may process signals from the entire array of ultrasound transducer elements. This may provide an improved accuracy of determining a location of the implant. The entire array of ultrasound transducer elements may also or alternatively be used when the implant is arranged far away from the array of ultrasound transducer elements such that all of the ultrasound transducer elements are able to receive signals of similar amplitude from the implant.

It should be realized that identifying a time point corresponding to a peak intensity may be achieved by determining the maximum (peak) intensity providing an indication of the point in time at which the maximum intensity is provided in the localization ultrasound signal. However, a representation of a time point corresponding to peak intensity need not be exactly tied to the maximum value of intensity. Rather, the time point may for instance be identified by processing the received localization ultrasound signal in a manner related to peak intensity. For instance, two separate moving averages of differently size time windows of the received localization ultrasound signal may be determined and a cross-point between the moving averages may be used as a representation of the peak intensity for identifying the time point of crossing of the moving averages as the time point corresponding to the peak intensity.

An ultrasound transducer element receiving the localization ultrasound signal first may be closest to the implant (unless obstructions are present between the implant and the array of ultrasound transducer elements). Hence, the identified time points provide an indication of relative distance between the ultrasound transducer elements and the implant. The identified time points provide information of relative time delays, which indicate the location of the implant to the ultrasound transducer elements, such that the relative time delays indicated by the identified time points form information of the location of the implant. However, the relative time delays may not necessarily provide information of an absolute location of the implant. For instance, a depth of the implant inside the body, i.e. a distance between the implant and the array of ultrasound transducer elements along a normal to the array may not necessarily be determined solely based on the relative time delays. However, the relative time delays may at least provide a direction in which the implant is displaced in relation to the array of ultrasound transducer elements, forming information relating to the location of the implant. The direction in which the implant is displaced may be very useful for controlling a direction into which a powering beam is transmitted such that powering of the implant may be efficiently performed.

Further, it should be realized that the array of ultrasound transducer elements need not necessarily be arranged in a fixed position. For instance, the array of ultrasound transducer elements may be arranged in a garment worn by a user, such that the array of ultrasound transducer elements may at least slightly change position with relation to the body. Thus, the device may be configured to determine information relating to a location of the implant in relation to the array of ultrasound transducer elements, such that the location information may be updated or changed by the array of ultrasound transducer elements moving while the implant is stationary within the body.

The array of ultrasound transducer elements may be used also for powering of the implant. Thus, determining information of the location of the implant in relation to the array of ultrasound transducer elements may be of high interest and it may be more relevant to determine a relative location of the implant to the array of ultrasound transducer elements than to determine an absolute location of the implant in the body.

According to an embodiment, ultrasound transducer elements of said array are further configured to transmit powering ultrasound signals towards the implant for powering the implant, wherein the ultrasound transducer elements are configured to output powering ultrasound signals with relative output delays of output of the powering ultrasound signals from the ultrasound transducer elements, wherein the relative output delays are reversed in relation to the relative time delays.

Thus, the ultrasound transducer elements may be used both for determining information of the location of the implant and for transmitting powering signals to the implant.

The direction of an ultrasound beam provided by ultrasound transducer elements may be controlled by controlling time delays between the signals output by the ultrasound transducer elements. Thus, the relative time delays indicated by the time points identified for the ultrasound transducer elements by processing the localization ultrasound signal may be reversed for controlling transmission of the powering ultrasound signals. This implies that the information relating to location of the implant need not even be processed to determine the location but rather may be immediately used for controlling the powering ultrasound signals. Hence, the powering ultrasound signals may be controlled in a very simple manner with very low processing requirements for controlling the output of the signals. Thus, control of output of the powering ultrasound signals is provided in a low power manner.

The device may be provided with a simple logic, which may be a digital logic, for transmitting the relative output delays to the ultrasound transducer elements. The simple logic may be easily implemented integrated with the array of ultrasound transducer elements and the signal processor in order to provide a compact device.

It should be realized that even if an unknown obstruction is present between the array of ultrasound transducer elements and the implant, the powering ultrasound signals may still efficiently power the implant. The obstruction may prevent correctly determining an absolute location of the implant. However, since the acquired information of relative time delays is directly used for controlling the output of the powering ultrasound signals, the powering ultrasound signals may unknowingly take such obstruction into account such as to efficiently power the implant.

The relative time delays being reversed implies that a difference in time of the relative output delay between two ultrasound transducer elements is the same as the difference in time of the relative time delay but the ultrasound transducer element which receives the localization ultrasound signal first among the two ultrasound transducer elements will output the powering ultrasound signal last among the two ultrasound transducer elements.

The device may be configured to transmit the powering ultrasound signals using the ultrasound transducer elements of said at least a subset of ultrasound transducer elements. Thus, the same subset of ultrasound transducer elements for which the relative time delays are determined may also be used for output of the powering ultrasound signals.

However, it should be realized that only a portion of the at least a subset of ultrasound transducer elements may be used for transmitting the powering ultrasound signals. For instance, ultrasound transducer elements which detect a very small intensity of the localization ultrasound signal need not be used in transmitting the powering ultrasound signal, since it may be determined that such ultrasound transducer elements provide a low contribution to powering of the implant.

According to an embodiment, the device further comprises a control unit for selecting ultrasound transducer elements to be included in the subset of ultrasound transducer elements.

This implies that the device is able to select ultrasound transducer elements to be used for detecting the localization ultrasound signal. Hence, the control unit may be configured to control power consumption of the device by selecting the ultrasound transducer elements to be included in the subset.

According to an embodiment, the control unit is configured to control a plurality of ultrasound transducer elements in the array to be active in a selection mode, wherein each ultrasound transducer element of the plurality of ultrasound transducer elements is configured to receive a selection ultrasound signal from the implant, wherein the control unit is further configured to select the ultrasound transducer elements to be included in the subset of ultrasound transducer elements based on signal strengths of the selection ultrasound signal received by the ultrasound transducer elements of the plurality of ultrasound transducer elements.

The device may thus use the selection mode to determine ultrasound transducer elements to be included in the subset for limiting power consumption. Thus, the selection mode provides input for determining the ultrasound transducer elements that are to be included in the subset.

The control unit may be configured to control some ultrasound transducer elements in the array to be active in the selection mode. Thus, the plurality of ultrasound transducer elements may only be a few of the ultrasound transducer elements in the array.

However, in some embodiments, the control unit may control all ultrasound transducer elements to be active in the selection mode. For instance, the selection mode may be used for determining the ultrasound transducer elements to be included in a subset, wherein the subset may be used for a relatively long time period for powering the implant. Thus, power consumption of the selection mode for determining the ultrasound transducer elements to be included in the subset may be relatively small compared to the power consumption during powering of the implant. Hence, it may in some embodiments be power efficient to use all or a large number of ultrasound transducer elements in the plurality of ultrasound transducer elements being active in the selection mode, such that the ultrasound transducer elements to be included in the subset may be determined based on accurate information.

The device may be configured to determine signal strengths detected by each of the active ultrasound transducer elements in the selection mode. This may be used for selecting ultrasound transducer elements to be included in the subset such that only ultrasound transducer elements that receive a relevant signal strength are included. The signal strength may be detected for instance as an intensity or an amplitude of the received selection ultrasound signal.

The selection of the ultrasound transducer elements to be included in the subset based on the signal strength may involve selecting ultrasound transducer elements based on the signal strength exceeding an absolute threshold or a relative threshold.

It should be realized that, according to an alternative embodiment, the device need not use any selection mode at all. For instance, the device may initially be configured to use all or a default subset of ultrasound transducer elements for receiving the localization ultrasound signal. Then, the localization ultrasound signal may be used both for determining signal strengths so as to determine ultrasound transducer elements to be included in the subset of ultrasound transducer elements for further exchanges of signals with the implant and for identifying time points indicating relative time delays for determining information relating to the location of the implant.

According to an embodiment, the control unit is configured to define a boundary of a region in which ultrasound transducer elements to be included in the subset of ultrasound transducer elements are arranged, wherein the boundary of the region is defined based on identifying ultrasound transducer elements in the plurality of ultrasound transducer elements that receive a signal strength of the selection ultrasound signal exceeding a predefined percentage of a maximum signal strength received among the plurality of ultrasound transducer elements.

Thus, a region may be determined in which the ultrasound transducer elements to be included in the subset are arranged. The region may correspond to a coherent area in a two-dimensional array or a line in a one-dimensional array. However, the region may alternatively correspond to multiple separate parts in the array, wherein the ultrasound transducer element in each part has received a signal strength exceeding the absolute or relative threshold.

Ultrasound transducer elements that receive a signal strength that is substantially smaller than a maximum signal strength received among the plurality of ultrasound transducer elements may only marginally contribute to accurately locating the implant. In addition, if the device is used for powering the implant, the ultrasound transducer elements that receive a low signal strength will not be able to substantially contribute to power received by the implant. Thus, power consumption may be reduced by not including ultrasound transducer elements in the subset which anyway will not contribute to accurately locating the implant and/or to powering the implant.

According to an embodiment, the control unit is configured to select all ultrasound transducer elements in the region to be included in the subset of ultrasound transducer elements.

The boundaries of the region may be determined based on information acquired in the selection mode. Thus, in the selection mode, it may be mainly desired to determine the boundaries of the region defining the subset of the ultrasound transducer elements. However, when the implant is to be localized and/or powered, all ultrasound transducer elements that receive a relatively strong signal strength may contribute to accurately locating the implant and/or to directing an ultrasound beam for efficiently powering the implant.

In most cases, the signal strength received by the ultrasound transducer elements is strictly decreasing with increasing distance from an ultrasound transducer element that receives the maximum signal strength. Hence, when boundaries of the region have been determined, it may be assumed that all ultrasound transducer elements within the region will receive a signal strength exceeding the predefined percentage of the maximum signal strength. Thus, selecting all ultrasound transducer elements in the region may imply that all ultrasound transducer elements that may substantially contribute to accurately locating and/or powering of the implant are selected.

According to an embodiment, the control unit is configured to control ultrasound transducer elements being spread apart to form part of the plurality of ultrasound transducer elements being active in the selection mode.

In the selection mode, information for selecting the ultrasound transducer elements to be included in the subset is acquired. In most cases, the signal strength received by the ultrasound transducer elements is strictly decreasing with increasing distance from an ultrasound transducer element that receives the maximum signal strength. Thus, the ultrasound transducer elements forming part of the plurality of ultrasound transducer being active in the selection mode may be sparsely arranged while still allowing the ultrasound transducer elements to be included in the subset to be accurately determined.

Thanks to using ultrasound transducer elements that are spread apart, power consumption in the selection mode may be limited. If a small number of ultrasound transducer elements form part of the plurality of ultrasound transducer elements, a coarse determination may be provided of the ultrasound transducer elements that will be able to contribute to accurately locating and/or to powering the implant. Thus, by increasing the number of ultrasound transducer elements forming part of the plurality of ultrasound transducer elements may allow a more accurate determination of the ultrasound transducer elements to be included in the subset at a cost of a higher power consumption in the selection mode.

The ultrasound transducer elements being spread apart implies that there are inactive ultrasound transducer elements arranged in the array between the ultrasound transducer elements being active and forming part of the plurality of ultrasound transducer elements. For instance, the ultrasound transducer elements forming part of the plurality of ultrasound transducer elements may be regularly arranged in the array, with a fixed number of inactive ultrasound transducer elements being arranged between two adjacent active ultrasound transducer elements in the array. Thus, for instance, less than 20%, such as less than 10% of the ultrasound transducer elements in the array may form part of the plurality of ultrasound transducer elements being active in the selection mode.

It should be realized that the ultrasound transducer elements need not necessarily be regularly arranged in the array. If the device has some information that indicates a more likely position of the implant, the ultrasound transducer elements forming part of the plurality of ultrasound transducer elements may be selected so as to provide more accurate information for regions of the array that are likely to be included in the subset and to provide more coarse information for other regions. For instance, the ultrasound transducer elements forming part of the plurality of ultrasound transducer elements may be selected based on a previous location of the implant. This also implies that neighboring ultrasound transducer elements in some parts of the array may form part of the plurality of ultrasound transducer elements. Hence, the ultrasound transducer elements being spread apart does not necessarily imply that some neighboring ultrasound transducer elements cannot form part of the plurality of ultrasound transducer elements.

According to an embodiment, each ultrasound transducer element of the plurality of ultrasound transducer elements is configured to receive a selection ultrasound signal that comprises a code for identifying that the selection ultrasound signal is emitted from the implant.

Thanks to receiving a selection ultrasound signal that comprises a code, robust detection of the selection ultrasound signal may be provided in relation to noise and/or reflections of the ultrasound signal. The device may be configured to process the selection ultrasound signal received and detected by the ultrasound transducer elements, wherein the device may identify the code in the detected selection ultrasound signal for identifying the selection ultrasound signal.

The code may for instance be included in the selection ultrasound signal as a modulation of the selection ultrasound signal. For instance, amplitude modulation may be provided to include the code in the selection ultrasound signal. The code may be digitally defined, e.g., by providing a high amplitude value to indicate a bit value of "1" and by providing a low amplitude value to indicate a bit value of "0" in the selection ultrasound signal. Thus, by providing a time sequence of amplitude modulation, a plurality of bits may be included in the selection ultrasound signal. For instance, the code may be at least 3 bits long to ensure a robust detection of the selection ultrasound signal.

It should be realized that a plurality of implants may be provided in the body of the living being. Then, different codes may be used for different implants to allow differentiating between a plurality of implants and allowing the device to monitor a plurality of implants. However, it should be realized that the code may be primarily used for robust detection of the selection ultrasound signal over noise and reflections.

It should further be realized that all ultrasound signals received by the ultrasound transducer elements may comprise the code identifying that the signal is emitted from the implant. Thus, the device may be configured to process all signals detected by the ultrasound transducer elements for identifying the code in the respective detected signals.

According to an embodiment, the device is configured to perform a selection update measurement for tracking ultrasound transducer elements to be included in the subset of ultrasound transducer elements, wherein the control unit is configured to control a second plurality of ultrasound transducer elements in the array to be active in an update mode, wherein the second plurality of ultrasound transducer elements include a first plurality of ultrasound transducer elements previously selected to be included in the subset of ultrasound transducer elements and one or more additional transducer elements adjacent to the first plurality of ultrasound transducer elements, wherein each ultrasound transducer element of the second plurality of ultrasound transducer elements is configured to receive a selection update ultrasound signal from the implant.

Thus, the device may be configured to track the implant. This implies that the location of the implant may be followed by providing a selection update measurement without need of using the plurality of ultrasound transducer elements spread apart the entire array for determining coarse information of a location of the implant.

The selection update measurement may be intermittently performed. For instance, the selection update measurement may be performed at regular intervals.

In an embodiment, the device is used for powering the implant. The device may thus receive the selection ultrasound signal using a small number of ultrasound transducer elements for determining the ultrasound transducer elements to be included in the subset. The device may further receive localization ultrasound signal using the subset for acquiring information of the location of the implant. The device may then use the subset of ultrasound transducer elements for outputting powering ultrasound signals to the implant. Intermittently, powering of the implant may be interrupted in order to perform a selection update measurement for tracking the implant.

The selection update measurement may be used for receiving and detecting the selection update ultrasound signal. The control unit may be configured to select the ultrasound transducer elements to be included in an updated subset of ultrasound transducer elements based on signal strengths of the selection update ultrasound signal received by the active ultrasound transducer elements in the update mode.

The selection update measurement may further be used to identify a time point corresponding to a peak intensity of the received selection update ultrasound signal at each active ultrasound transducer element, providing indication of relative time delays between the time points identified for the ultrasound transducer elements. The relative time delays thus form information relating to a location of the implant. The device may further be configured to determine the relative time delays based on the identified time points for the ultrasound transducer elements selected to be included in the updated subset. The device may be configured to use the relative time delays for controlling the ultrasound transducer elements selected to be included in the updated subset such that the ultrasound transducer elements are configured to output powering ultrasound signals with relative output delays of output of the powering ultrasound signals from the ultrasound transducer elements, wherein the relative output delays are reversed in relation to the determined relative time delays for the selection update ultrasound signal.

In the update mode, the control unit may allow increasing the number of ultrasound transducer elements to be included in the subset based on using one or more additional transducer elements adjacent to the first plurality of ultrasound transducer elements. The additional transducer elements may be immediate neighbors to the ultrasound transducer elements at a boundary of a region in which the first plurality of transducer elements is arranged. For instance, one ultrasound transducer element may be added at the boundary in each row and/or column of the array. However, it should be realized that more than one additional ultrasound transducer element may be added at the boundary to enable more quickly increasing the number of ultrasound transducer elements to be included in the subset.

However, it should be realized that the device need not necessarily use the update mode. For instance, the implant may be configured to change position very slowly, if at all. The device may be used for intermittently determining location of the implant and for powering the implant. The device may then be configured to, each time the implant is to be located and powered, initially determine the ultrasound transducer elements to be included in the subset based on the selection mode and then determine information of the location of the implant and perform powering of the implant for a desired period of time.

According to an embodiment, the control unit is further configured to select the ultrasound transducer elements to be included in the subset of ultrasound transducer elements based on signal strengths of the selection update ultrasound signal received by the ultrasound transducer elements of the second plurality of ultrasound transducer elements.

Thus, the selection update ultrasound signal may be used for ensuring that an appropriate subset of the ultrasound transducer elements is used for tracking the location of the implant.

For instance, the device may be configured to compare the signal strengths received by additional ultrasound transducer elements at opposite sides of the region defined by the first plurality of transducer elements. This may be used for ensuring that the implant may be followed, while the implant moves in relation to a plane defined by the array of ultrasound transducer elements. It also requires very limited processing, since only the signal strengths between the ultrasound transducer elements in a pair (or a few pairs) of elements need to be compared to find which signal strength is larger.

However, it should be realized that the selection of the ultrasound transducer elements to be included in the subset based on the selection update measurement may be performed in different manners. For instance, a threshold of the signal strength may be defined, e.g., based on a maximum signal strength received during the selection mode. Then, the signal strengths received by ultrasound transducer elements at the boundary of the region within the first plurality of the transducer elements as well as the signal strengths received by the additional ultrasound transducer elements may be compared to the threshold. The ultrasound transducer elements receiving a signal strength above the threshold may be included in the subset. Thus, the number of ultrasound transducer elements included in the subset may be increased or decreased based on the selection update ultrasound signal and the region of the ultrasound transducer elements within the array may be moved for tracking movement of the implant.

The selection of the ultrasound transducer elements to be included in the subset based on the selection update measurement may be performed in a corresponding manner as described in the selection mode of the device. Thus, the signal strengths of all of the ultrasound transducer elements in the second plurality of ultrasound transducer elements may be processed to define the ultrasound transducer elements to be included in the subset based on identifying ultrasound transducer elements in the second plurality of ultrasound transducer elements that receive a signal strength of the selection update ultrasound signal exceeding a predefined percentage of a maximum signal strength received among the second plurality of ultrasound transducer elements.

According to an embodiment, the array of ultrasound transducer elements is configured to transmit a plurality of initial powering ultrasound signals into a plurality of directions for scanning a medium in which the implant is arranged, wherein the plurality of initial powering ultrasound signals is configured to provide power to the implant allowing the implant to output the localization ultrasound signal.

The implant may not have any battery or other element for storing energy between different sessions of communication with the device. Thus, the device may need to initially power the implant before the implant may output the selection ultrasound signal and/or the localization ultrasound signal.

The implant may comprise an energy storing element, which may be configured to store energy at least during a brief time period. For instance, the implant may comprise a capacitor which may receive and at least temporarily store power from the powering ultrasound signals allowing the implant to transmit ultrasound signals.

The array of ultrasound transducer elements may thus be configured to transmit powering ultrasound signals for scanning the medium such that the implant will receive energy. The initial powering ultrasound signals may be used for allowing the implant to be powered so as to be able to output a single selection ultrasound signal and a single localization ultrasound signal. The device may be configured to determine information based on these signals to allow the device to efficiently power the implant to provide further power to the implant.

The device may for instance be used for powering the implant each time it is desired that a measurement be performed by the implant in the body of the living being. Thus, the implant may be triggered by the device to perform a measurement and may further communicate measurement results to the device.

The procedure of locating, tracking, and powering the implant may be repeated each time a measurement is to be performed.

According to an embodiment, the array of ultrasound transducer elements is configured to transmit and receive ultrasound signals in a frequency range of 500 kHz MHz.

Ultrasound signals in this frequency range may be suitable for transmitting and receiving ultrasound signals between the device and the implant.

Ultrasound signals having a low frequency may provide a larger penetration depth in tissue compared to ultrasound signals having a high frequency. Thus, the frequency of the ultrasound signals may be selected to be sufficiently low so as to provide a desired penetration depth.

Ultrasound signals having a high frequency may provide accurate control of direction of the ultrasound allowing the ultrasound signals to be accurately focused on a desired spatial position. Thus, the frequency of the ultrasound signals may be selected to be sufficiently high so as to provide a desired control of focus of the ultrasound signals. This may be utilized for providing efficient powering of the implant by ensuring that the energy output by the device is efficiently focused on a location in which the implant is arranged.

According to an embodiment, the device comprises a carrier configured to be attached to a body in which the implant is arranged.

The array of ultrasound transducer elements may be arranged on the carrier. The processor may also be arranged on the carrier.

This implies that the device may be worn on the body of the living being in which the implant is implanted. Hence, the device facilitates being continuously used for monitoring the implant.

The carrier may be directly attached to the body. For instance, the carrier may be attached to a surface of the body, such as to skin. The carrier may comprise an adhesive patch which may be attached to the skin of the body. According to an alternative, the carrier may be attached to the body by being arranged around a part of the body, such as being arranged around an arm or around the torso.

According to an alternative embodiment, the device may be configured to be arranged so as to facilitate ultrasound signals to be received and/or transmitted between the implant and the device. For instance, the device may comprise a carrier which may be embedded in a garment for allowing the array of ultrasound transducer elements to be arranged in contact with the body. Alternatively, the device may comprise a carrier, which may be embedded in a chair or a seat allowing the array of ultrasound transducer elements to be arranged in contact with the body when a person with the implant sits in the chair or seat.

According to a second aspect, there is provided a method for monitoring an implant, said method comprising: receiving a localization ultrasound signal from an implant using at least a subset of an array of ultrasound transducer elements; for each ultrasound transducer element in the subset, identifying a time point corresponding to a peak intensity of the received localization ultrasound signal at the ultrasound transducer element wherein relative time delays between the time points identified for the ultrasound transducer elements form information relating to a location of the implant.

Effects and features of this second aspect are largely analogous to those described above in connection with the first aspect. Embodiments mentioned in relation to the second aspect are largely compatible with the first aspect.

Thanks to using peak intensity in the received localization ultrasound signal, the device allows time points representing receipt of the localization ultrasound signal to be robustly determined for the ultrasound transducer elements. Also, simple processing is required such that the time points may be identified using analog processing of the localization ultrasound signal received and detected by the ultrasound transducer elements. This implies that power consumption may be limited.

The identified time points provide information relating to the location of the implant. However, according to an embodiment, the method may further comprise determining the relative time delays between the time points identified for the ultrasound transducer elements.

According to an embodiment, the method further comprises: transmitting, by the ultrasound transducer elements in the subset, powering ultrasound signals towards the implant for powering the implant, wherein powering ultrasound signals of the ultrasound transducer elements are output with relative output delays, wherein the relative output delays are reversed in relation to the relative time delays.

Thus, the method may use the same ultrasound transducer elements both for determining information of the location of the implant and for transmitting powering signals to the implant. Thanks to using the relative output delays that are reversed in relation to the relative time delays, control for directing the powering signals towards the implant may be implemented in a very simple manner. Further, thanks to the powering ultrasound signals being controlled, the method may provide efficient powering of the implant as the energy output by the ultrasound transducer elements may be directed towards the location of the implant.

According to an embodiment, the method may further comprise receiving a selection ultrasound signal from the implant using a plurality of ultrasound transducer elements being active in a selection mode, and selecting ultrasound transducer elements to be included in the subset based on signal strengths of the selection ultrasound signal received by the ultrasound transducer elements of the plurality of ultrasound transducer elements.

Thus, the method may use a selection ultrasound signal for determining which ultrasound transducer elements should be used for locating the implant and, optionally, powering of the implant. This allows the ultrasound transducer elements to be included in the subset to be efficiently selected. Further, thanks to using only some of the ultrasound transducer elements in locating of the implant and, optionally, powering of the implant, power consumption may be limited.

According to another embodiment, the method may further comprise performing a selection update measurement for tracking ultrasound transducer elements to be included in the subset of ultrasound transducer elements, wherein a second plurality of ultrasound transducer elements in the array is controlled to be active in an update mode, wherein the second plurality of ultrasound transducer elements includes a first plurality of ultrasound transducer elements previously selected to be included in the subset of ultrasound transducer elements and one or more additional transducer elements adjacent to the first plurality of ultrasound transducer elements, wherein each ultrasound transducer element of the second plurality of ultrasound transducer elements is configured to receive a selection update ultrasound signal from the implant.

The selection update measurement may thus be used for updating the ultrasound transducer elements to be included in the subset such that a location of the implant may be tracked. In addition, the selection update measurement may be configured to update information of relative time delays for updating information relating to location of the implant. Further, the updated information of the relative time delays may be used for controlling transmission of powering ultrasound signals such that the powering ultrasound signals are focused on the updated location of the implant.

BRIEF DESCRIPTION OF THE DRAWINGS

The above, as well as additional objects, features, and advantages of the present description, will be better understood through the following illustrative and non-limiting detailed description, with reference to the appended drawings. In the drawings like reference numerals will be used for like elements unless stated otherwise.

FIG. 3 is a flowchart of a method according to an embodiment.

DETAILED DESCRIPTION

Figure 1:
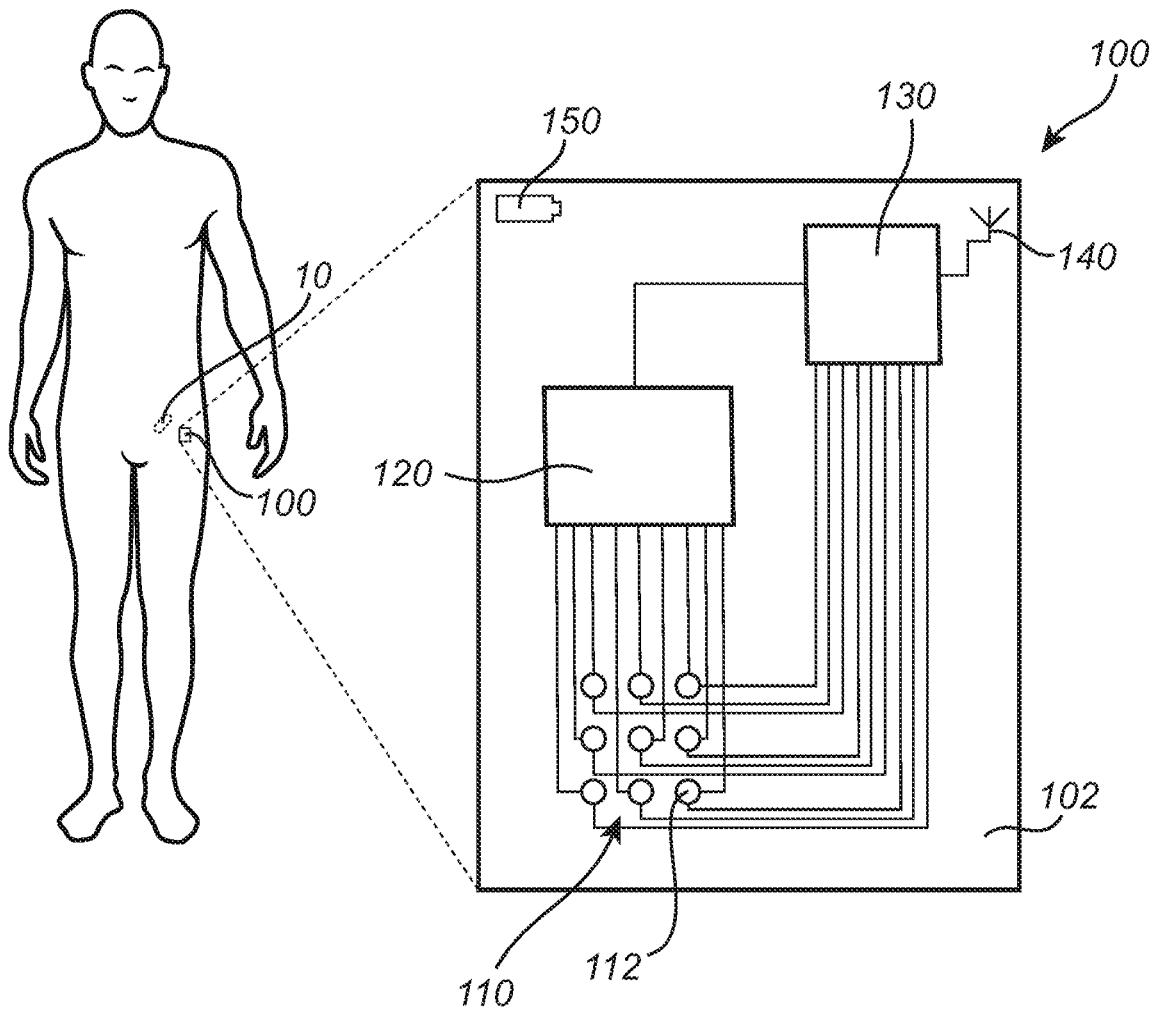
FIG. 1 is a schematic view of a device according to an embodiment.

FIG. 1 illustrates an implant 10 being arranged in a body of a living being, here shown as being arranged in a human being. FIG. 1 further illustrates a device 100 configured to monitor the implant 10. FIG. 1 also shows a schematic magnification of the device 100 to facilitate illustration of components of the device 100.

The device 100 is shown to be attached to skin of the human being. The device 100 may thus comprise a carrier 102 which may be configured to be attached to skin. For instance, the carrier 102 may be provided in form of an adhesive patch. However, it should be realized that the device 100 may be arranged in many alternative ways in relation to the human being having the implant 10, such as the device 100 being arranged in a garment worn by the human being. It should also be realized that the device 100 may also be implanted in the body, such as being mounted on an external surface of an organ in which the implant 10 is arranged.

The device 100 comprises an array 110 of ultrasound transducer elements 112. The ultrasound transducer elements 112 may be arranged such that the ultrasound transducer elements 112 make contact with the body when the device 100 is to be used. For instance, the ultrasound transducer elements 112 may be arranged on a surface of a carrier 102 such that when the carrier 102 is attached to the body, the ultrasound transducer elements 112 face the body and make contact therewith. The ultrasound transducer elements 112 being arranged to make contact with the body implies that the ultrasound transducer elements 112 may have a good coupling to the body for transmitting ultrasound signals into the body towards the implant 10 and receiving ultrasound signals propagating in the body from the implant 10.

The ultrasound transducer elements 112 may be configured to receive and transmit ultrasound signals. The ultrasound transducer element 112 may be configured to detect a received ultrasound signal by converting an ultrasound signal sensed by the ultrasound transducer element 112 to a corresponding electrical signal. Similarly, the ultrasound transducer element 112 may be configured to convert a received electrical signal to an ultrasound signal being output by the ultrasound transducer element 112. The ultrasound transducer element 112 may be configured in any manner for converting ultrasound signals to electrical signals and vice versa. For instance, the ultrasound transducer element 112 may comprise a diaphragm sensitive to vibrations of the ultrasound signal, wherein detected vibrations may be converted to an electrical signal using capacitance, piezoelectricity, or an optical signal. The ultrasound transducer element 112 may be a capacitive micromachined ultrasonic transducer, a piezoelectric micromachined ultrasonic transducer, an optical micromachined ultrasound sensor, or a bulk-driven piezoelectric transducer. Other alternatives may be used as realized by the person skilled in the art.

Attenuation of ultrasound in biological tissue is related to frequency of ultrasound such that a lower frequency has a lower attenuation. Hence, it may be desired to use a low frequency of ultrasound. However, half power beam width (HPBW) of an ultrasound beam is inversely proportional to the frequency of ultrasound. Thus, in order to allow focusing of an ultrasound beam in a small volume, such as onto an implant 10 having a size in order of millimeters, it is desired to have a high frequency of ultrasound. Taking the above considerations into account, the ultrasound transducer elements 112 in the array 110 may be configured to transmit and receive ultrasound signals in a frequency range of 500 kHz-10 MHz, such as a frequency range of 700 kHz-2 MHz, such as approximately 1 MHz. This may be suitable for providing a penetration depth above 100 mm, such as approximately 125 mm.

A pitch of the ultrasound transducer elements 112 in the array corresponds to a distance between centers of neighboring ultrasound transducer elements 112 and hence is a sum of a size of each ultrasound transducer elements 112 and a spacing between the neighboring elements. The pitch may affect grating lobes, crosstalk, and spatial peak temporal average intensity of the acoustic field of the ultrasound signals. The grating lobes increase with pitch, such that maximum pressure that may be delivered by the array 110 reduces for higher pitch. Crosstalk refers to a degree a signal is affected due to adjacent ultrasound transducer elements 112 and is relevant when calculating relative delays of signals as will be described below. The crosstalk may tend to increase with a shorter spacing between neighboring elements.

The pitch may suitably be selected in a range of λ/2 to λ, where λ is a wavelength of ultrasound in the biological tissue. The wavelength is dependent on speed of ultrasound in the biological tissue and frequency of the ultrasound. For 1 MHz frequency, the wavelength is approximately 1.65 mm. The size of the ultrasound transducer elements 112 may be approximately equal to a spacing between the ultrasound transducer elements 112.

The penetration depth in the biological tissue to which power can be delivered by ultrasound by the array 110 of ultrasound transducer elements 112 is directly proportional to a size of the array 110. For a one-dimensional array, the maximum penetration depth is approximately 2.5 times a size of the array 110, where the size of the array 110 is defined as a total size of the ultrasound transducer elements 112. Thus, the size w of the array may be defined as:

$$w = N * (\text{pitch} - \text{spacing}),$$

where N is the number of ultrasound transducer elements 112 in the array 110, pitch is the pitch of the array 110 and spacing is the spacing between neighboring ultrasound transducer elements 112. The size may further be set to $$w = d/2.5,$$

where d is a maximum penetration depth to be provided by the array 110.

It should be realized that using the size as discussed above for each dimension of a two-dimensional array 110 may imply that a higher power is delivered to the implant 10.

Further, it should be realized that the device 100 may be used for receiving and/or transmitting ultrasound signals to an implant 10 that changes position in relation to the device 100.

The device 100 further comprises a signal processor 120. The signal processor 120 may be connected to the array 110 of ultrasound transducer elements 112 for receiving detected ultrasound signals from the array 110 of ultrasound transducer elements 112. The signal processor 120 may thus be electrically connected to the ultrasound transducer elements 112 for receiving electrical signals formed by the ultrasound transducer elements 112 in response to the ultrasound signal being incident on the ultrasound transducer elements 112.

The signal processor 120 may be configured to process the analog electrical signals. The signal processor 120 may comprise passive components (such as capacitors, resistors, and inductors) and/or active components (such as transistors and operational amplifiers) in order to process electrical signals. The device 100 may be configured to require simple processing of the received ultrasound signals such that the signal processor 120 may be implemented as an analog signal processor 120. However, it should be realized that the signal processor 120 may be configured to process digital signals and/or that output from an analog signal processor 120 may further be converted to digital format for further processing in digital format.

The signal processor 120 may be directly electrically connected to the array 110 of ultrasound transducer elements 112. For instance, the signal processor 120 may be integrated with the array 110 of ultrasound transducer elements 112 on a common substrate, such as on a common chip, which may further be mounted on the carrier 102.

The signal processor 120 may comprise separate portions of processor circuitry, each portion being dedicated to process signals received from a single ultrasound transducer element 112.

The device 100 may further comprise a control unit 130. The control unit 130 may be configured to control functionality of the array 110 of ultrasound transducer elements 112 and/or the signal processor 120. For instance, the control unit 130 may control which ultrasound transducer elements 112 that are active to receive and detect ultrasound signals and/or to transmit ultrasound signals.

The control unit 130 may further be configured to receive signals that have been processed by the signal processor 120 or receive information from the signal processor 120 based on the signal processing performed by the signal processor 120, such that the control unit 130 may further process the signals or the information received. For instance, the control unit 130 may be configured to control functionality of the array 110 of ultrasound transducer elements 112 and/or the signal processor 120 based on processing of signals or information received from the signal processor 120.

The control unit 130 may be arranged in a common housing with the array 110 of ultrasound transducer elements 112 and the signal processor 120. However, according to an alternative, the control unit 130 may be arranged separately from the array 110 of ultrasound transducer elements 112 and the signal processor 120 and may be configured to communicate with the ultrasound transducer elements 112 and/or the signal processor 120 through wired or wireless communication.

The control unit 130 may for instance be arranged in the same housing with the array 110 of ultrasound transducer elements 112 and the signal processor 120 by being arranged on the same carrier 102. The control unit 130 may for instance be integrated on a common chip with the array 110 of ultrasound transducer elements 112 and the signal processor 120, or arranged on a common support surface, such as on a common circuit board.

According to an alternative, the control unit 130 may be arranged in a server "in the cloud" and may be configured to communicate with the array 110 of ultrasound transducer elements 112 and/or the signal processor 120 through a computer or telecommunication network, such as the Internet.

The control unit 130 may be a central processing unit (CPU), which may execute the instructions of one or more computer programs in order to provide desired functionality.

The control unit 130 may alternatively be implemented as firmware arranged e.g. in an embedded system, or as a specifically designed processing unit, such as an Application-Specific Integrated Circuit (ASIC) or a Field-Programmable Gate Array (FPGA), which may be configured to implement desired functionality.

The device 100 may further comprise a wireless communication unit 140 within the housing. This implies that the control unit 130 may be configured to communicate with an external unit, for example, for sharing data and for receiving instructions. The device 100 may be configured to communicate with the external unit through a computer or telecommunication network, such as the Internet, or via a wireless signal, such as using Bluetooth®.

The device 100 may for instance be configured to communicate with a mobile phone or a smart watch of the user having the implant 10, allowing the user to be provided with information obtained from the implant 10.

The device 100 may further comprise a battery 150 for powering the device 100. The battery 150 may be rechargeable for ensuring long lifetime of the device 100.

The device 100 may be particularly useful for monitoring an implant 10 such that ultrasound signals may be transmitted between the implant 10 and the device 100 through biological media that is heterogenous, however, not excessively scattering. This enables use of the device 100 for monitoring the implant 10 being arranged relatively deep within the body, while the device 100 is arranged externally to the body, attached to skin. For instance, the device 100 may be used for monitoring implants 10 for organs like the urinary bladder, liver, stomach, intestines, etc. However, it should be realized that other applications may also feasible, for instance, if the device 100 may be arranged relatively close to the implant 10.

Figure 2:
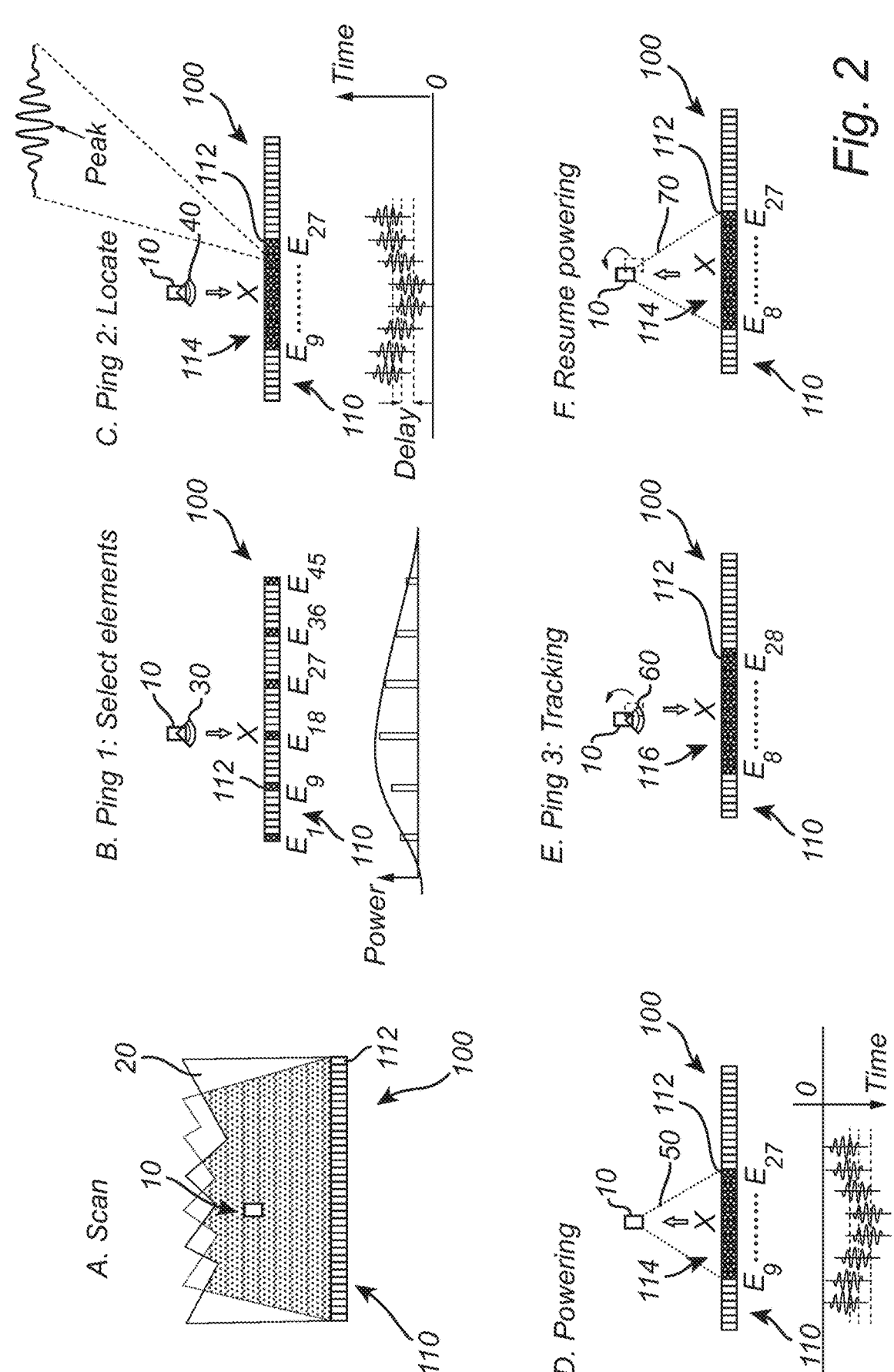
FIG. 2 is a schematic view illustrating different steps for localizing, powering, and tracking of an implant using the device.

Referring now to FIG. 2, transmission of ultrasound signals between the array 110 of ultrasound transducer elements 112 and the implant 10 according to an embodiment will be described. In FIG. 2, a one-dimensional array 110 is illustrated for simplicity. It should be realized that a two-dimensional array 110 may be used instead.

It should be realized that all of the ultrasound signals described below need not be used in all use cases of the implant 10 and the device 100.

In the embodiment illustrated in FIG. 2, the implant 10 is initially depleted of energy. Thus, the implant 10 may initially need to be powered to allow transmission of ultrasound signals from the implant 10. Further, a location of the implant 10 within the body is also considered to initially not be known. For instance, this may be due to the implant 10 and the device 100 not having communicated for a relatively long period of time, or that the implant 10 and the device 100 communicate for a first time.

Thus, in a first phase, illustrated in part A of FIG. 2, the array 110 of ultrasound transducer elements 112 is configured to transmit a plurality of initial powering ultrasound signals 20 into a plurality of directions for scanning the medium in which the implant 10 is arranged. The plurality of initial powering ultrasound signals 20 is configured to provide power to the implant 10 allowing the implant 10 to output an ultrasound signal in response.

The control unit 130 may control output of the initial powering ultrasound signals 20. The control unit 130 may control the array 110 for setting a focus depth of the powering ultrasound signals 20 to slightly over the largest possible penetration depth where the implant 10 can still be powered (e.g., 130 mm for a 125 mm maximum penetration depth), and for performing a two-dimensional scan of a plane at the focus depth with a step size corresponding to the HPBW of the output ultrasound beams. Independent of the location of the implant 10 within the three-dimensional volume in which powering ultrasound signals 20 are output, the scanning of the powering ultrasound signals 20 will ensure that the implant 10 receives energy through the powering ultrasound signals 20. The implant 10 may receive enough energy to execute transmission of two ultrasound signals as explained below.

As soon as the implant 10 has received a minimum amount of energy, the implant 10 may transmit a selection ultrasound signal 30 back to the array 110 of ultrasound transducer elements 112, as illustrated in part B of FIG. 2. The selection ultrasound signal 30 may be provided in form of a short, predetermined packet (Ping1).

Thus, during the initial scanning of the powering ultrasound signals 20, the array 110 of ultrasound transducer elements 112 may be configured to output a powering ultrasound signal 20 in one direction and may then be configured to listen to determine if the predetermined packet of Ping1 is received, before proceeding to transmit a following powering ultrasound signal 20 in a slightly different direction.

The array 110 of ultrasound transducer elements 112 may be set in a selection mode when listening for Ping1. The control unit 130 may be configured to control a plurality of ultrasound transducer elements 112 to be active in the selection mode. To save power, only a small number of ultrasound transducer elements 112 may form part of the plurality of ultrasound transducer elements 112 and be used for receiving the selection ultrasound signal.

The control unit 130 may be configured to control ultrasound transducer elements 112 that are spread apart to form part of the plurality of ultrasound transducer elements being active in the selection mode. This implies that the array 110 of ultrasound transducer elements 112 may be configured to coarsely identify a location of the implant 10 so as to determine which ultrasound transducer elements 112 should be used for determining the location of the implant 10 more accurately.

The ultrasound transducer elements 112 that are active in the selection mode may be placed equidistantly throughout the array 110 as illustrated in part B of FIG. 2, wherein the active elements are shown with dark shading. If the implant 10 is expected to be arranged at a deep penetration depth, it makes sense to listen to Ping1 using all ultrasound transducer elements 112. However, if the implant 10 is expected to be arranged at a shallower penetration depth, it may be favorable from a power efficiency perspective to not use all the ultrasound transducer elements 112, since not all of them will contribute adequately (>5%) to the total received power at the device 100.

The selection ultrasound signal 30 may comprise a code for identifying that the selection ultrasound signal is emitted from the implant 10. Thus, by the code being provided within the selection ultrasound signal 30, the selection ultrasound signal 30 may be robustly identified over noise and/or reflections. The selection ultrasound signal 30 may comprise a short packet, wherein the implant 10 transmits an ultrasound signal for a period of time. The ultrasound signal may be amplitude modulated in order to encode the ultrasound signal with the code for identifying the selection ultrasound signal 30. The selection ultrasound signal 30 may thus provide digital information for transmitting the code to the device 100.

A high amplitude of the transmitted ultrasound signal may indicate a value of "1", whereas a low amplitude of the transmitted ultrasound signal may indicate a value of "0". The amplitude may be held for a predetermined time duration, which is interpreted as corresponding to one bit by the implant 10 and the device 100.

Thus, Ping1 may comprise three initial bits providing the code for identifying that the selection ultrasound signal is emitted from the implant 10. Further, Ping1 may comprise four additional bits, during which the selection ultrasound signal 30 is transmitted with a high amplitude to ensure that a strong signal may be detected by the array 110 of ultrasound transducer elements 112. The three initial bits may, however, be formed by both high and low amplitudes, such as the code being provided by three bits representing 1-0-1.

The array 110 of ultrasound transducer elements 112 may be configured to receive the selection ultrasound signal 30 that comprises the code. Signals detected by the ultrasound transducer elements 112 may be processed in analog domain by the signal processor 120 to identify that the code is received. However, the ultrasound signal may further be passed to a digital processing circuitry for identifying the code being received in digital domain.

The ultrasound transducer elements 112 in the plurality of ultrasound transducer elements being active in the selection mode may receive the selection ultrasound signal 30. The signal processor 120 may be configured to determine signal strengths of the selection ultrasound signal 30 received by each of the ultrasound transducer elements 112 in the plurality of ultrasound transducer elements 112, as illustrated in the graph in part B of FIG. 2. The signal strengths may be determined as an amplitude of the received acoustic field or as an intensity of the acoustic field. It should be realized that the amplitude is proportional to the intensity, which in turn is representative of a power received by the ultrasound transducer element 112.

A peak signal strength may be determined for each of the ultrasound transducer elements 112 being active in the selection mode. For instance, a maximum amplitude of the received selection ultrasound signal 30 may be determined. The maximum signal strength received among the plurality of ultrasound transducer elements 112 being active may thus be determined. In absence of scattering media, the ultrasound transducer element 112 that receives the selection ultrasound signal 30 first is the element being arranged closest to the implant 10. This element will also have the maximum amplitude.

The signal strengths that are received by the ultrasound transducer elements 112 being active are compared to the maximum signal strength. The ultrasound transducer elements 112 for which a received signal strength is above a threshold in relation to the maximum signal strength may be selected for being used in localization of the implant 10, and/or in powering and/or in tracking of the implant 10.

For instance, the received signal strength may be compared to a predefined percentage of the maximum signal strength. In an embodiment, ultrasound transducer elements 112 that receive a peak amplitude which is larger than 25% of the maximum signal strength (more than 6% of received intensity) may be selected for being further used.

The signal strength may be expected to strictly decrease from an ultrasound transducer element receiving the maximum signal strength towards ultrasound transducer elements being at an increasing distance from the element that receives the maximum signal strength. Thus, the ultrasound transducer elements 112 that receive a sufficient signal strength may be used for defining a boundary of a region in the array 110 of ultrasound transducer elements 112 such that the ultrasound transducer elements 112 within the region may be expected to receive a sufficient signal strength. Thus, the boundary may be defined by the ultrasound transducer elements 112 being farthest away from the element that receives maximum signal strength, while still receiving a signal strength exceeding the predefined percentage.

However, it should be realized that the region of the array 110 that receive sufficient signal strength may comprise a plurality of separate parts, for instance if the ultrasound signal travels in scattering media between the implant 10 and the ultrasound transducer elements 112. Thus, boundaries for each part of the region may be defined.

The control unit 130 may be configured to select ultrasound transducer elements 112 to be included in a subset 114 of ultrasound transducer elements 112. The control unit 130 may perform this selection based on the signal strengths received by the ultrasound transducer elements 112 being active in the selection mode as described above.

As mentioned, boundaries of a region may be defined based on the signal strengths. The control unit 130 may be configured to select all ultrasound transducer elements 112 within the region or all ultrasound transducer elements 112 within each part of the region. The control unit 130 may set the ultrasound transducer elements 112 that are selected to be included in the subset 114 of ultrasound transducer elements 112 to be active for receiving a further ultrasound signal. The other ultrasound transducer elements 112 may be switched off in order to save power.

It should be realized that the ultrasound transducer elements 112 to be included in the subset 114 may be determined in alternative ways, not necessarily using the selection mode. For instance, a subset 114 of ultrasound transducer elements 112 may be immediately determined based on an expected location of the implant 10, such as based on a previous location of the implant 10 from previous sessions of monitoring the implant 10.

In addition, the ultrasound transducer elements 112 to be included in the subset 114 may be determined based on a timing of receipt of a selection ultrasound signal 30. The ultrasound transducer elements 112 that receive the selection ultrasound signal 30 first will be arranged closest to the implant 10 and may hence contribute most to determining accurate information of the location of the implant 10 and to providing energy to the implant 10 if the implant 10 is to be powered by the device 100.

Also, the device 100 may be configured to select a minimum number of ultrasound transducer elements 112 to form part of the subset 114. This minimum number may be related to a minimum penetration depth in tissue that is desired for an ultrasound signal that is to provide powering of the implant 10. Thus, if the number of ultrasound transducer elements 112 based on the signal strengths determined in the selection mode is too small, the number of ultrasound transducer elements 112 to be included in the subset 114 may be increased in order to ensure that at least the minimum number of ultrasound transducer elements 112 is selected.

For instance, the minimum number of ultrasound transducer elements 112 to be included in the subset may be defined based on a minimum size $w_m$ formed by the ultrasound transducer elements 112 of the subset, which may be defined as:

$$w_m = \frac{0.88 \times \lambda d_m}{l_a},$$

where $d_m$ is a minimum penetration depth to be provided and $l_a$ is a desired location accuracy of the implant 10, wherein the location accuracy can be defined by HPBW of ultrasound beams output by the ultrasound transducer elements 112.

Then, the implant 10 may be configured to transmit a localization ultrasound signal 40 as illustrated in part C of FIG. 2. Thus, the power received by the implant 10 based on the initial powering ultrasound signal 20 may be used by the implant 10 for transmitting the selection ultrasound signal 30 and the localization ultrasound signal 40.

The localization ultrasound signal 40 may comprise a code in a same manner as described above for the selection ultrasound signal. The localization ultrasound signal may be provided in the form of a short, predetermined packet (Ping2).

The array 110 of ultrasound transducer elements 112 is configured to receive the localization ultrasound signal from the implant 10. As indicated in part C of FIG. 2, the subset 114 of ultrasound transducer elements 112, which may be selected based on the selection ultrasound signal 30 as described above, may be active to detect the localization ultrasound signal 40.

The signal processor 120 is configured to identify a time point corresponding to a peak intensity of the received localization ultrasound signal at each ultrasound transducer element 112 in the subset 114, as indicated in the graph in part C of FIG. 2. It should be realized that for illustrative purposes, the time points are not illustrated immediately below corresponding ultrasound transducer elements 112. The signal processor 120 may further configured to determine relative time delays between the time points identified for the ultrasound transducer elements 112. Alternatively, the signal processor 120 may pass information of the identified time points to another processor, such as digital processing circuitry for determining the relative time delays. The digital processing circuitry may form part of the control unit 130 or may be implemented in a separate processing unit for processing information from the signal processor 120.

The relative time delays form information relating to a location of the implant 10 since the relative time delays represent a difference in distance between respective ultrasound transducer elements 112 and the implant 10.

Thus, instead of recording a value of the peak amplitude, the signal processor 120 may record a timestamp for each ultrasound transducer element 112 where the received acoustic field peaks. The relative time delays may then be determined for each ultrasound transducer element 112 with respect to the element that receives the highest peak (and earliest timestamp). Alternatively, relative time delays may be determined for adjacent ultrasound transducer elements 112, such that a relative time delay for each ultrasound transducer element 112 may be determined in relation to the timestamp for a closest neighboring ultrasound transducer element 112.

The determination of time points corresponding to peak intensities of the received localization ultrasound signal for determining relative time delays may avoid any discrepancies in determination of the information of location of the implant 10, for instance, due to spurious firing of the implant 10, or unwanted low intensity reflections at beginning or at end of receipt of the localization ultrasound signal.

The device 100 may use the relative time delays for controlling the device 100 to provide efficient powering of the implant 10. The relative time delays may be used for steering powering ultrasound signals transmitted by the subset of ultrasound transducer elements 112 so as to focus energy onto the location of the implant 10.

Once the relative time delays are determined, the array 110 of ultrasound transducer elements 112 may switch back from a receiving mode to a power radiation mode, illustrated in part D of FIG. 2. The ultrasound transducer elements 112 that are selected to be included in the subset 114 are actuated. The ultrasound transducer elements 112 in the subset 114 are thus configured to transmit powering ultrasound signals towards the implant 10 for powering the implant. The ultrasound transducer elements 112 are controlled to output the powering ultrasound signals with relative output delays of the powering ultrasound signals from the ultrasound transducer elements 112 for forming a combined powering ultrasound signal 50 focused on the implant 10. The relative output delays of the ultrasound transducer elements 112 are reversed in relation to the determined relative time delays, as illustrated in the graph in part D of FIG. 2.

This may ensure good beamforming of the ultrasound signal received at the implant 10 and the control of the beamforming is provided in a very simple manner by just reversing the determined relative time delays. The elements that do not contribute adequately to received power at the implant 10 (e.g., due to shadowing, scattering or long physical distance) are not activated, which ensures decent overall system energy efficiency.

The device 100 may be configured to provide powering of the implant 10 during a period of time such that the implant 10 may receive sufficient power for performing desired actions. For instance, the implant 10 may be powered in order to allow measurements to be performed in the body and to allow measurement results to be communicated to the device 100 or to another external device.

Each ultrasound transducer element 112 may be configured to output a powering ultrasound signal at a set maximum power. The maximum power may be controlled in relation to regulations of allowed peak acoustic pressure and peak acoustic intensity that may be delivered to a human being.

It should be realized that the power being provided by the ultrasound transducer elements 112 may be controlled such that the maximum power is not necessarily used. For instance, if a large number of ultrasound transducer elements 112 are included in the subset 114, the ultrasound transducer elements 112 may be controlled to transmit a power below the maximum power. In addition, all of the ultrasound transducer elements 112 in the subset 114 need not necessarily transmit an identical power.

As described above, the device 100 may be used for determining information of location of the implant 10 in order to allow the device 100 to efficiently provide power to the implant 10. The device 100 may thus transmit the powering ultrasound signal 50 for a period of time in order to power the implant 10. However, the device 100 may only be able to continue providing power in an energy-efficient manner in static conditions.

The implant 10 and/or the device 100 may move slightly. In addition, parameters, such as multipath parameters, for ultrasound signal transmission through tissue between the device 100 and the implant 10 may change. This implies that there may be a need to update parameters for controlling the powering ultrasound signal 50.

Thus, at regular intervals, such as every 10 ms, power transmission by the device 100 may be interrupted in order to allow for determination of information of location of the implant 10 for updating the parameters. The device 100 may thus use a tracking mode for regularly updating information of the location of the implant 10.

When the power transmission by the device 100 is interrupted, the device 100 may be set in an update mode, wherein the device 100 is configured to perform a selection update measurement for tracking ultrasound transducer elements 112 to be included in the subset 114 of ultrasound transducer elements 112. The subset 114 may thus be updated in order to allow efficient powering of the implant and/or to allow following the location of the implant 10.

The implant 10 is configured to transmit a selection update ultrasound signal 60, as illustrated in part E of FIG. 2. The selection update ultrasound signal 60 may comprise a code in a same manner as described above for the selection ultrasound signal 30. The selection update ultrasound signal 60 may be provided in form of a short, predetermined packet (Ping3).

It should be realized that the implant 10 may be configured to transmit identical ultrasound signals when transmitting the selection ultrasound signal 30, the localization ultrasound signal 40 and the selection update ultrasound signal 60. Thus, the use of different names of these signals should not be construed as necessarily implying that the signals are different in content. However, the device 100 may process the signals differently in order to obtain different information from the signals. The different names are mainly used in order to differentiate between the signals being received and processed by the device 100.

The subset 114 of ultrasound transducer elements 112 determined based on the localization ultrasound signal 40 may form a first plurality of ultrasound transducer elements 112. The control unit 130 may be configured to control a second plurality 116 of ultrasound transducer elements 112 in the array to be active in the update mode. The second plurality 116 of ultrasound transducer elements 112 includes the first plurality of ultrasound transducer elements 112 previously selected to be included in the subset 114 of ultrasound transducer elements 112 and one or more additional ultrasound transducer elements 112 adjacent to the first plurality of ultrasound transducer elements 112.

The additional ultrasound transducer elements 112 may be immediate neighbors to the ultrasound transducer elements 112 of the first plurality of ultrasound transducer elements 112 at a boundary of the region in which the first plurality of transducer elements 112 is arranged. For instance, one ultrasound transducer element 112 may be added at the boundary in each row and/or column of the array 110. However, it should be realized that more than one additional ultrasound transducer element 112 may be added at the boundary to enable more quickly increasing the number of ultrasound transducer elements 112 to be included in the subset 114 or following larger displacements of the of the implant 10 in relation to the device 100.

Movement of organs inside the body of the human being can be as low as 1 mm/5 ms. In embodiments, the array 110 may have a pitch of approximately 1 mm, and it may therefore be sufficient to include only 1 additional ultrasound transducer element 112, as illustrated in part E of FIG. 2, at each side of the first plurality of ultrasound transducer elements 112 for receiving the selection update ultrasound signal 60.

The ultrasound transducer elements 112 of the second plurality of ultrasound transducer elements 112 may be configured to receive the selection update ultrasound signal 60. Signals detected by the ultrasound transducer elements 112 may be processed by the signal processor 120 and/or digital processing circuitry to identify that the code is received in order to ensure that the signal is robustly received.

The signal processor 120 may further be configured to determine signal strengths of the selection update ultrasound signal 60 received by each of the ultrasound transducer elements 112 in the second plurality 116 of ultrasound transducer elements 112. The control unit 130 is further configured to select the ultrasound transducer elements 112 to be included in the subset 114 of ultrasound transducer elements 112 based on signal strengths of the selection update ultrasound signal 60 received by the ultrasound transducer elements 112 of the second plurality 116 of ultrasound transducer elements 112.

For instance, the signal strengths received by the additional ultrasound transducer elements 112 at opposite sides of the region defined by the first plurality of transducer elements may be compared. The element receiving a larger signal strength may be selected to form part of the subset 114 of ultrasound transducer elements 112 to be used for further powering of the implant 10 and/or following of the location of the implant 10.

This requires very limited processing for updating the ultrasound transducer elements 112 to be part of the subset 114, since only the signal strengths between the ultrasound transducer elements in a pair (or a few pairs) of elements need to be compared to find which signal strength is larger.

However, it should be realized that the selection of the ultrasound transducer elements 112 to be included in the subset 114 based on the selection update measurement may be performed in different manners. For instance, the selection may be made in a same manner as described above in relation to the selection mode, such that the signal strengths received by each ultrasound transducer element 112 is compared to a maximum signal strength received by the ultrasound transducer element receiving a strongest signal. Then, the number of ultrasound transducer elements 112 included in the subset 114 may be increased or decreased based on the selection update ultrasound signal 60 and the region of the ultrasound transducer elements 112 within the array 110 may be moved for tracking movement of the implant 10.

In addition, the signal processor 120 may be configured to identify a time point corresponding to a peak intensity of the received selection update ultrasound signal 60 at each ultrasound transducer element 112 in the second plurality 116 of ultrasound transducer elements 112. Similar to the processing of the localization ultrasound signal 40, the signal processor 120 may further be configured to determine relative time delays between the time points identified for the ultrasound transducer elements 112 or the digital processing circuitry may be configured to determine the relative time delays. This implies that the relative time delays may also be updated in the update mode.

Once the relative time delays are determined, the array 110 of ultrasound transducer elements 112 may switch back from a receiving mode to a power radiation mode, illustrated in part F of FIG. 2. The ultrasound transducer elements 112 that are selected to be included in the subset 114 based on the selection update measurement are actuated. The ultrasound transducer elements 112 in the subset 114 are thus configured to transmit powering ultrasound signals towards the implant 10 for powering the implant 10. The ultrasound transducer elements 112 are controlled to output the powering ultrasound signals with relative output delays of the powering ultrasound signals from the ultrasound transducer elements 112 for forming a combined powering ultrasound signal 70 focused on the implant 10 at the updated location of the implant 10. The relative output delays of the ultrasound transducer elements 112 are reversed in relation to the determined relative time delays.

Thus, parameters for powering of the implant 10 may be updated to allow maintaining an energy-efficient powering of the implant 10.

Referring now to FIG. 3, a method for monitoring of an implant will be briefly summarized. The method may be performed by a device comprising an array of ultrasound transducer elements.

The method may comprise transmitting 202 by an array of ultrasound transducer elements initial powering ultrasound signals into a plurality of directions in a body of a living being for scanning the medium in which an implant is arranged. The plurality of initial powering ultrasound signals is configured to provide power to the implant allowing the implant to output at least one ultrasound signal in response.

The method may further comprise receiving 204 a selection ultrasound signal from the implant. A plurality of ultrasound transducer elements may be active to receive the selection ultrasound signal. The ultrasound transducer elements being part of the plurality of ultrasound transducer elements may be spread apart across the array to allow coarsely determining a location of the implant 10.

The method may further comprise selecting 206 ultrasound transducer elements to be included in a subset of ultrasound transducer elements for receiving a localization ultrasound signal from the implant. The ultrasound transducer elements may be selected based on received signal strengths of the selection ultrasound signal.

The method further comprises receiving 208 a localization ultrasound signal from the implant 10 using at least the subset of ultrasound transducer elements, according to the selection based on the selection ultrasound signal. It should be realized that the method need not necessarily include receiving of the selection ultrasound signal. In such case, all of the ultrasound transducer elements may be configured to receive the localization ultrasound signal. Alternatively, the ultrasound transducer elements included in the subset may be selected based on other information on the location of the implant, such as a location of the implant during a previous session of communication between the device and the implant.

The method further comprises for each ultrasound transducer element in the subset, identifying 210 a time point corresponding to a peak intensity of the received localization ultrasound signal at the ultrasound transducer element.

The method may further comprise determining 212 relative time delays between the time points identified for the ultrasound transducer elements. The relative time delays form information relating to a location of the implant. The relative time delays between two ultrasound transducer elements provide information of a difference in distance between each of the ultrasound transducer elements, respectively, and the implant.

The relative time delays may be used for controlling powering of the implant by the array of ultrasound transducer elements. Thus, the method may further comprise transmitting 214, by the ultrasound transducer elements in the subset, powering ultrasound signals towards the implant for powering the implant. The powering ultrasound signals of the ultrasound transducer elements are output with relative output delays, wherein the relative output delays are reversed in relation to the determined relative time delays. This implies that the powering ultrasound signals may form a combined powering ultrasound signal which is focused on the location of the implant for providing efficient powering of the implant.

The method may further comprise performing 216 a selection update measurement for tracking ultrasound transducer elements to be included in the subset of ultrasound transducer elements. The transmission of the powering ultrasound signals may thus be interrupted in order to allow the device to perform the selection update measurement.

A second plurality of ultrasound transducer elements in the array is controlled to be active in an update mode for performing the selection update measurement. The second plurality of ultrasound transducer elements includes a first plurality of ultrasound transducer elements previously selected to be included in the subset of ultrasound transducer elements and one or more additional transducer elements adjacent to the first plurality of ultrasound transducer elements. Each ultrasound transducer element of the second plurality of ultrasound transducer elements is configured to receive a selection update ultrasound signal from the implant.

The received selection update ultrasound signal may be processed for updating the ultrasound transducer elements to be included in the subset based on signal strengths received by the ultrasound transducer elements in the second plurality of ultrasound transducer elements. The selection update measurement may thus be used for updating the ultrasound transducer elements to be included in the subset such that a location of the implant may be tracked.

In addition, the received selection update ultrasound signal may be processed for each ultrasound transducer element to be included in the subset, to identify a time point corresponding to peak intensity of the received selection update ultrasound signal at the ultrasound transducer element, and to determine relative time delays between the identified time points. Thus, the selection update measurement may provide updated information of relative time delays for updating information relating to location of the implant.

The method may further comprise resuming 218 transmission, by the ultrasound transducer elements in the updated subset, powering ultrasound signals towards the implant for powering the implant. The powering ultrasound signals of the ultrasound transducer elements are output with relative output delays, wherein the relative output delays are reversed in relation to the determined relative time delays based on the updated information. This implies that the powering ultrasound signals may form a combined powering ultrasound signal which is focused on the updated location of the implant for providing efficient powering of the implant.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A device for monitoring an implant; said device comprising:
   an array of ultrasound transducer elements configured to receive a localization ultrasound signal from the implant and transmit powering ultrasound signals towards the implant for powering the implant;
   a signal processor configured to, for each ultrasound transducer element of at least a subset of ultrasound transducer elements, identify a time point corresponding to a peak intensity of the received localization ultrasound signal at the ultrasound transducer element, wherein relative time delays between the time points identified for the ultrasound transducer elements form information relating to a location of the implant, and
   wherein the subset of ultrasound transducer elements is further configured to transmit the powering ultrasound signals towards the implant for powering the implant, with relative output delays, wherein the relative output delays are reversed in relation to the relative time delays.

2. The device according to claim 1, wherein the device further comprises a control unit for selecting ultrasound transducer elements to be included in the subset of ultrasound transducer elements.

3. The device according to claim 2, wherein the control unit is configured to control a plurality of ultrasound transducer elements in the array to be active in a selection mode, wherein each ultrasound transducer element of the plurality of ultrasound transducer elements is configured to receive a selection ultrasound signal from the implant, wherein the control unit is further configured to select the ultrasound transducer elements to be included in the subset of ultrasound transducer elements based on signal strengths of the selection ultrasound signal received by the ultrasound transducer elements of the plurality of ultrasound transducer elements.

4. The device according to claim 3, wherein the control unit is configured to define a boundary of a region in which ultrasound transducer elements to be included in the subset of ultrasound transducer elements are arranged, wherein the boundary of the region is defined based on identifying ultrasound transducer elements in the plurality of ultrasound transducer elements that receive a signal strength of the selection ultrasound signal exceeding a predefined percentage of a maximum signal strength received among the plurality of ultrasound transducer elements.

5. The device according to claim 4, wherein the control unit is configured to select all ultrasound transducer elements in the region to be included in the subset of ultrasound transducer elements.

6. The device according to claim 3, wherein the control unit is configured to control ultrasound transducer elements being spread apart to form part of the plurality of ultrasound transducer elements being active in the selection mode.

7. The device according to claim 3, wherein each ultrasound transducer element of the plurality of ultrasound transducer elements is configured to receive a selection ultrasound signal that comprises a code for identifying that the selection ultrasound signal is emitted from the implant.

8. The device according to claim 2, wherein the device is configured to perform a selection update measurement for tracking ultrasound transducer elements to be included in the subset of ultrasound transducer elements, wherein the control unit is configured to control a second plurality of ultrasound transducer elements in the array to be active in an update mode, wherein the second plurality of ultrasound transducer elements include a first plurality of ultrasound transducer elements previously selected to be included in the subset of ultrasound transducer elements and one or more additional transducer elements adjacent to the first plurality of ultrasound transducer elements, wherein each ultrasound transducer element of the second plurality of ultrasound transducer elements is configured to receive a selection update ultrasound signal from the implant.

9. The device according to claim 8, wherein the control unit is further configured to select the ultrasound transducer elements to be included in the subset of ultrasound transducer elements based on signal strengths of the selection update ultrasound signal received by the ultrasound transducer elements of the second plurality of ultrasound transducer elements.

10. The device according to claim 1, wherein the array of ultrasound transducer elements is configured to transmit a plurality of initial powering ultrasound signals into a plurality of directions for scanning a medium in which the implant is arranged, wherein the plurality of initial powering ultrasound signals is configured to provide power to the implant allowing the implant to output the localization ultrasound signal.

11. The device according to claim 1, wherein the array of ultrasound transducer elements is configured to transmit and receive ultrasound signals in a frequency range of 500 kHz-10 MHz.

12. The device according to claim 1, wherein the device comprises a carrier configured to be attached to a body in which the implant is arranged.

13. A method for monitoring an implant, said method comprising:

receiving a localization ultrasound signal from an implant using at least a subset of an array of ultrasound transducer elements;

for each ultrasound transducer element in the subset, identifying a time point corresponding to a peak intensity of the received localization ultrasound signal at the ultrasound transducer element, wherein relative time delays between the time points identified for the ultrasound transducer elements form information relating to a location of the implant; and transmitting, by the ultrasound transducer elements in the subset, powering ultrasound signals towards the implant for powering the implant, wherein powering ultrasound signals of the ultrasound transducer elements are output with relative output delays, wherein the relative output delays are reversed in relation to the relative time delays.

* * * * *